(12) United States Patent
Sakaguchi et al.

(10) Patent No.: US 10,188,562 B2
(45) Date of Patent: Jan. 29, 2019

(54) DISPOSABLE DIAPER AND A METHOD OF MANUFACTURING A DISPOSABLE DIAPER

(71) Applicant: UNICHARM CORPORATION, Shikokuchuo-shi, Ehime (JP)

(72) Inventors: Satoru Sakaguchi, Kanonji (JP); Yasuhiro Yamanaka, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 1070 days.

(21) Appl. No.: 14/397,139

(22) PCT Filed: Apr. 25, 2013

(86) PCT No.: PCT/JP2013/062250
§ 371 (c)(1),
(2) Date: Oct. 24, 2014

(87) PCT Pub. No.: WO2013/161957
PCT Pub. Date: Oct. 31, 2013

(65) Prior Publication Data
US 2015/0119841 A1    Apr. 30, 2015

(30) Foreign Application Priority Data

Apr. 27, 2012  (JP) ................................. 2012-103376

(51) Int. Cl.
*A61F 13/15*  (2006.01)
*A61F 13/20*  (2006.01)
(Continued)

(52) U.S. Cl.
CPC ...... *A61F 13/515* (2013.01); *A61F 13/15203* (2013.01); *A61F 13/15593* (2013.01);
(Continued)

(58) Field of Classification Search
CPC .......... A61F 13/15203; A61F 13/15593; A61F 13/15756; A61F 13/49017; A61F 13/515
See application file for complete search history.

(56) References Cited

U.S. PATENT DOCUMENTS 4,081,301 A    3/1978  Buell
4,695,278 A *  9/1987  Lawson ............ A61F 13/49017
                                            604/385.24
(Continued)

FOREIGN PATENT DOCUMENTS

EP    1166727 A2    1/2002
JP    57-26219 B2   6/1982
(Continued)

OTHER PUBLICATIONS

Office Action in AU Application No. 2013253466, dated Dec. 1, 2016.
(Continued)

*Primary Examiner* — Michele M Kidwell
(74) *Attorney, Agent, or Firm* — Hauptman Ham, LLP (57) ABSTRACT

A disposable diaper includes a skin-surface side sheet; a non-skin surface side sheet; an absorber; and a waistline retaining unit. Leg stretching units are arranged in the inner side in a longitudinal direction from diaper ends that configure the outer circumference of the disposable diaper or the inner side in a widthwise direction from the diaper ends. A part of the waistline retaining unit is arranged in at least one of a first region in an outer side in the longitudinal direction from the ends of the leg stretching units, and a second region in an outer side in the widthwise direction from the ends of the leg stretching units. A joint region where the skin-surface side and non-skin surface side sheets are joined is provided along the diaper ends in at least one of a first region and a second region.

10 Claims, 4 Drawing Sheets

(51) Int. Cl.
*A61F 13/515* (2006.01)
*A61F 13/49* (2006.01)
*A61F 13/58* (2006.01)

(52) U.S. Cl.
CPC .. *A61F 13/15756* (2013.01); *A61F 13/49017* (2013.01); *A61F 13/58* (2013.01); *A61F 2013/15406* (2013.01); *A61F 2013/49074* (2013.01)

(56) References Cited

U.S. PATENT DOCUMENTS

| | | | | |
|---|---|---|---|---|
| 4,909,803 | A | * | 3/1990 | Aziz ................ A61F 13/49001 604/385.28 |
| 5,151,092 | A | * | 9/1992 | Buell ................ A61F 13/15593 604/358 |
| 5,196,000 | A | * | 3/1993 | Clear ................ A61F 13/49009 604/358 |
| H1420 | H | * | 2/1995 | Richardson ............ A61F 13/16 604/358 |
| 6,453,628 | B2 | | 9/2002 | Traxler |
| 2002/0052591 | A1 | | 5/2002 | Zehner et al. |
| 2012/0297605 | A1 | | 11/2012 | Gouda et al. |

FOREIGN PATENT DOCUMENTS

| | | |
|---|---|---|
| JP | 11-502427 A | 3/1999 |
| JP | 2011-156123 A | 8/2011 |
| JP | 2012-34810 A | 2/2012 |
| JP | 2013-230210 A | 11/2013 |
| WO | 03/030774 A2 | 4/2003 |

OTHER PUBLICATIONS

International Search Report dated Jul. 16, 2013 in International Application No. PCT/JP2013/062250 filed Apr. 25, 2013.
Japanese Office Action dated Feb. 19, 2013 in corresponding Japanese Application No. 2012-103376 filed Apr. 27, 2012.
Office Action dated Oct. 6, 2015, corresponding to Japanese Patent Application No. 2013-119696.
Extended European Search Report in EP Application No. 13782527.9, dated Dec. 23, 2015.
Office Action dated Jul. 2, 2015, corresponding to Chinese patent application No. 201380022255.1.

* cited by examiner

DISPOSABLE DIAPER AND A METHOD OF MANUFACTURING A DISPOSABLE DIAPER

RELATED APPLICATIONS

The present application is a National Phase of International Application Number PCT/JP2013/062250, filed Apr. 25, 2013, which claims priority to Japanese Application Number 2012-103376, filed Apr. 27, 2012.

TECHNICAL FIELD

The present invention relates to a disposable diaper and a method of manufacturing a disposable diaper.

BACKGROUND ART

Conventionally, there is known a disposable diaper having: a front waistline region; a rear waistline region; a crotch region; a pair of leg hole openings; an absorber running across the crotch region and extending to the front waistline region and rear waistline region; and leg stretching units stretching in a product longitudinal direction and arranged along the leg hole openings. The leg stretching units are arranged only near the leg hole openings and not in the entire region of the disposable diaper in longitudinal direction.

In Patent Literature 1, a method of manufacturing a disposable diaper in which the leg stretching units are arranged only near the leg hole openings is disclosed. According to the method of manufacturing the disposable diaper of Patent Literature 1, a first web configuring either one of the topsheet and the backsheet of the disposable diaper is conveyed in a continuous state, and an adhesive for pasting elastic members is applied near the leg hole openings of the first web (the portion where the leg stretching units are provided). The elastic members configuring the leg stretching units are elongated in the product longitudinal direction in a continuous state, and the elastic members in the elongated state are arranged on the first web. Subsequently, a second web configuring the other one of the topsheet and the backsheet is pasted on the first web and the elastic members.

In this way, a continuous body of continuous first web, second web, and elastic members arranged between the two webs is manufactured. Next, the continuous body is cut along the product widthwise direction in each of individual product lengths. As a result, the elastic members in the elongated state are constricted in the product longitudinal direction, and only the portion that is pasted near the leg hole openings by the adhesive remains. Thus, the leg stretching units can be provided only near the leg hole openings.

CITATION LIST

Patent Literature

[PTL 1] Japanese Patent Publication No. S57 (1982)-26219

SUMMARY OF INVENTION

However, the above-described disposable diaper had the below problems.

In the above-described disposable diaper, elastic members are pasted on the web in an arrangement region of leg stretching units. However, in the other regions, in order to shrink the elastic members after cutting the continuous body, the elastic members are not pasted on the web. Therefore, in the region where the elastic members are arranged in the manufacturing stage and the elastic members are not arranged in the product state, that is, in the outer side in the product longitudinal direction or the outer side in the product widthwise direction from the leg stretching units, an adhesive cannot be applied on the first web and the second web in order to set the leg stretching units in a shrinkable state. Thus, the first web and the second web are not pasted in the product state on the outer side in the product longitudinal direction or the outer side in the product widthwise direction from the leg stretching units.

Furthermore, in the so-called tape-type disposable diaper, a fastening tape is provided in the rear waistline region, and a target unit for affixing the fastening tape is provided in the front waistline region. As a result of engagement between the fastening tape and the target unit, the disposable diaper is retained along the waistline of the wearer. Thus, a pulling force works in the product widthwise direction on the fastening tape, the target unit, and a waistline retaining unit that includes the region extending in the product widthwise direction from the fastening tape and the target unit.

The waistline retaining unit is arranged in the outer side in the product longitudinal direction or the outer side in the product widthwise direction from the leg hole openings, and is the region where the topsheet and the backsheet may not be pasted together. Thus, since the topsheet and the backsheet of the waistline retaining unit are not pasted together, the force is applied only to one of the sheets at the time of being pulled. For example, when a relatively high load is exerted, such as at the time of putting on or wearing the disposable diaper, a force that is stronger than the strength of one of the sheets works on the sheets because of which the sheets may tear.

Thus, the present invention has been achieved in view of the above problems, and an object thereof is to provide a disposable diaper with which the strength of the waistline retaining unit that holds the waistline of the wearer in a so-called tape-type disposable diaper is increased, and the tearing at the time of putting on or wearing the diaper can be prevented, and also to provide a method of manufacturing such a disposable diaper.

The disposable diaper (disposable diaper 10) according to the present disclosure is summarized as a disposable diaper, including: a front waistline region (front waistline region 20); a rear waistline region(rear waistline region 30); a crotch region (crotch region 25) positioned between the front waistline region and the rear waistline region; a product longitudinal direction(product longitudinal direction L) from the front waistline region towards the rear waistline region, and a product widthwise direction (product widthwise direction W) perpendicular to the product longitudinal direction; a skin-surface side sheet (skin-surface side sheet 50) arranged at a skin contact surface side of a wearer; a non-skin surface side sheet (non-skin surface side sheet 51) arranged at a non-skin contact surface side of the skin-surface side sheet; an absorber (absorber 40) arranged between the skin-surface side sheet and the non-skin surface side sheet, running across the crotch region, and extending from the crotch region to at least either one of the front waistline region and rear waistline region; a waistline retaining unit holding the disposable diaper onto the body of the wearer in the front waistline region and the rear waistline region; and leg stretching units (leg stretching unit 75) arranged along leg hole openings (leg hole opening 35) provided in an outer side in the product widthwise direction from the absorber and expand and contract along the product longitudinal direction, wherein the leg stretching units are arranged between the skin-surface side sheet and the non-skin surface side sheet, and are arranged in the inner side in the product longitudinal direction from diaper ends that configure the outer circumference of the disposable diaper or the inner side in the product widthwise direction from the diaper ends in a plan view, and a part of the waistline retaining unit is arranged in at least one of a first region (first region R1) in an outer side in the product longitudinal direction from the ends of the leg stretching units in the product longitudinal direction, and a second region (second region R2) in an outer side in the product widthwise direction from the ends of the leg stretching units in the product longitudinal direction, and a joint region (joint region 65) where the skin-surface side sheet and the non-skin surface side sheet are joined is provided along the diaper ends in at least one of a first region and a second region .

The method of manufacturing a disposable diaper according to the present disclosure is summarized as method of manufacturing a disposable diaper, including: a front waistline region, a rear waistline region, a crotch region positioned between the front waistline region and the rear waistline region; a product longitudinal direction from the front waistline region towards the rear waistline region, and a product widthwise direction perpendicular to the product longitudinal direction; a skin-surface side sheet arranged at a skin contact surface side of the wearer; and a non-skin surface side sheet arranged at a non-skin contact surface side of the topsheet; and an absorber arranged between the skin-surface side sheet and the non-skin surface side sheet, running across the crotch region, and extending from the crotch region to at least either one of the front waistline region and rear waistline region; and leg stretching units arranged along leg hole openings provided in an outer side in the product widthwise direction from the absorber and can expand and contract along the product longitudinal direction, the method comprising: a step of continuously conveying a first web that configures either one of the skin-surface side sheet and the non-skin surface side sheet; a step of elongating, the elastic members configuring the leg stretching units, in a continuous state, in the product longitudinal direction; a step of cutting, the elastic members that are in the elongated state, along the product widthwise direction; a step of pasting, the elastic members that are in the cut state, on the first web through an adhesive; and a step of affixing, a second web that configures the other one of the skin-surface side sheet and the non-skin surface side sheet, on the first web and the elastic members through an adhesive.

DESCRIPTION OF EMBODIMENTS

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Overall Schematic Configuration of Disposable Diaper

Figure 1:
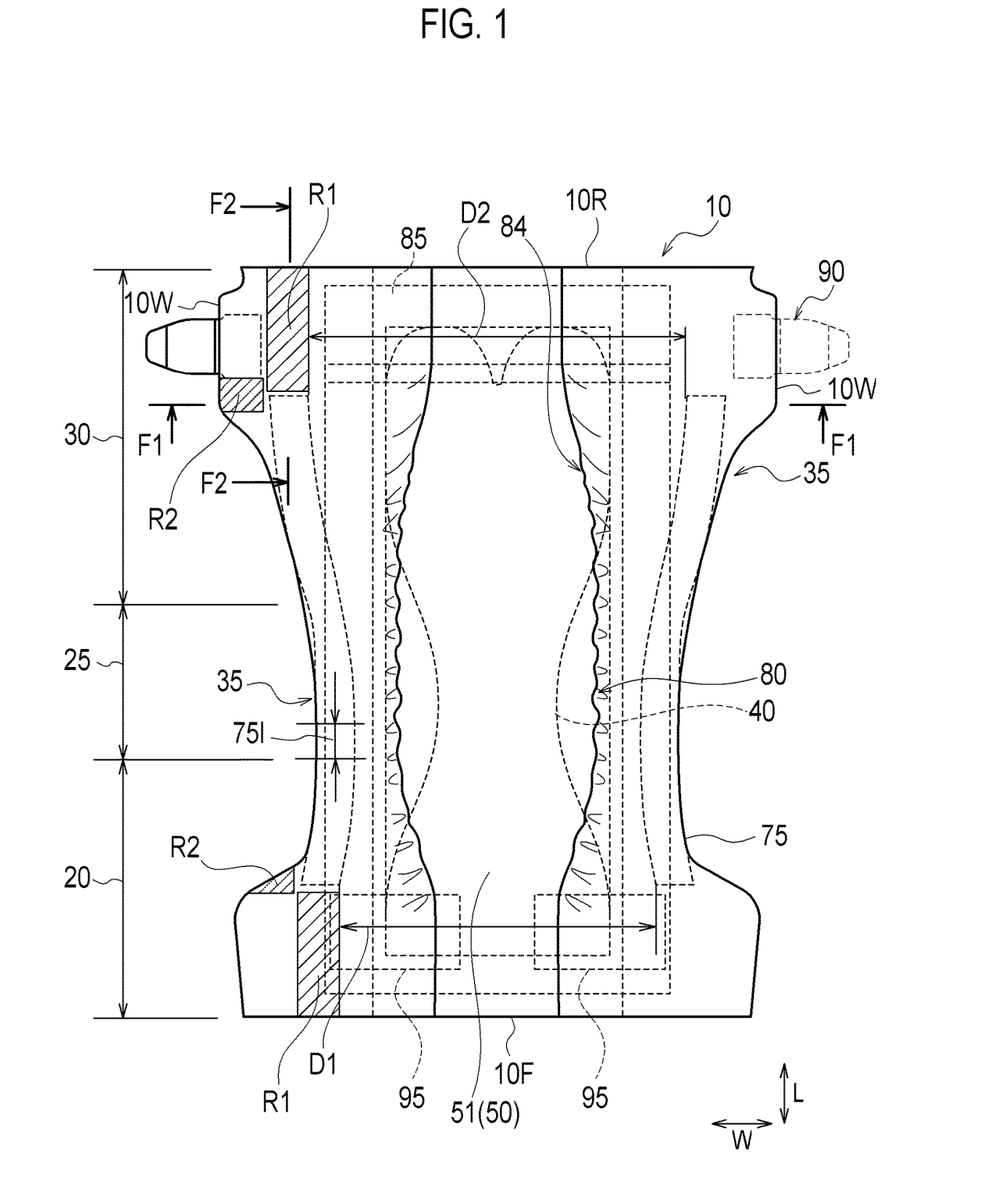
FIG. 1 is an exploded plan view of a disposable diaper according to the present embodiment.
Figure 2:
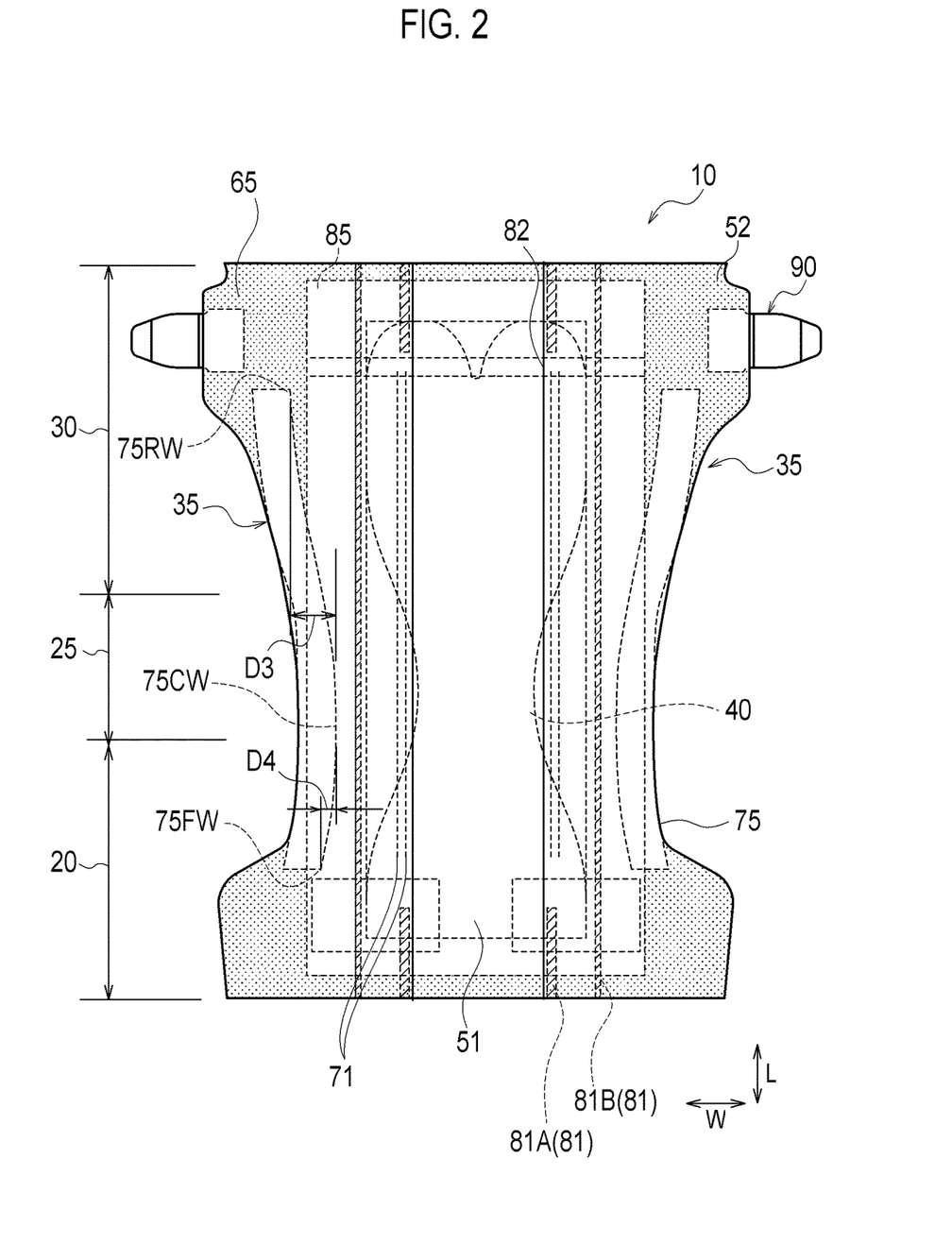
FIG. 2 is an exploded plan view of the disposable diaper according to the present embodiment.
Figure 3:
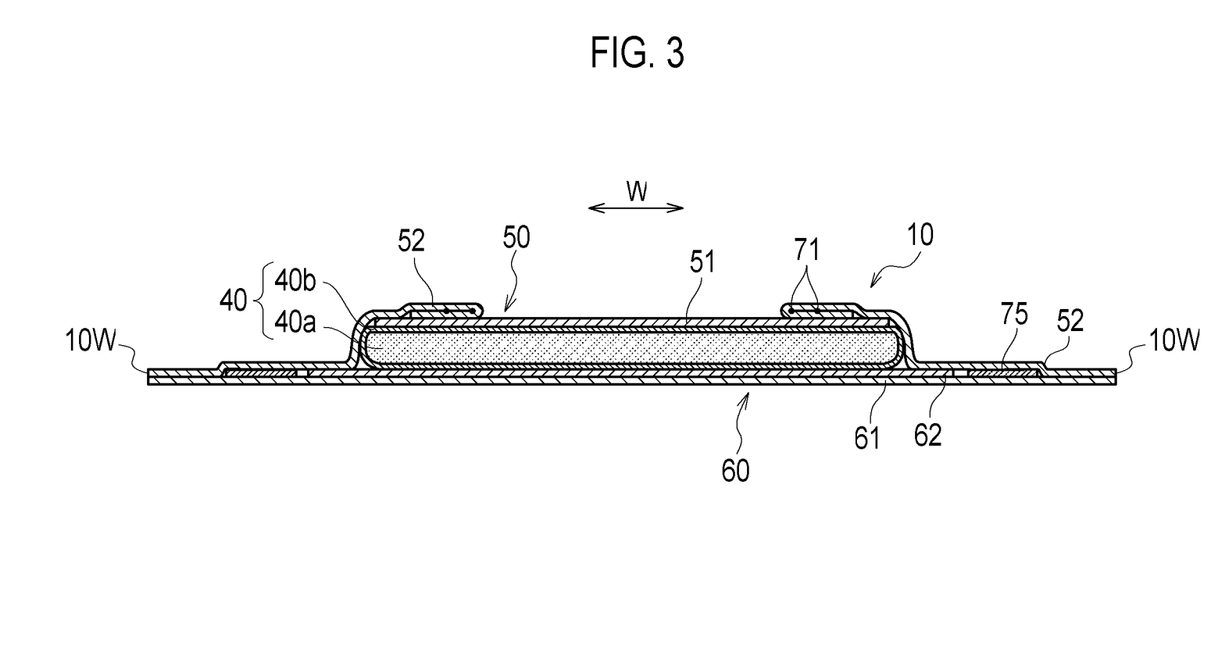
FIG. 3 is a cross-sectional view of the disposable diaper along an F1-F1 line shown in FIG. 1.
Figure 4:
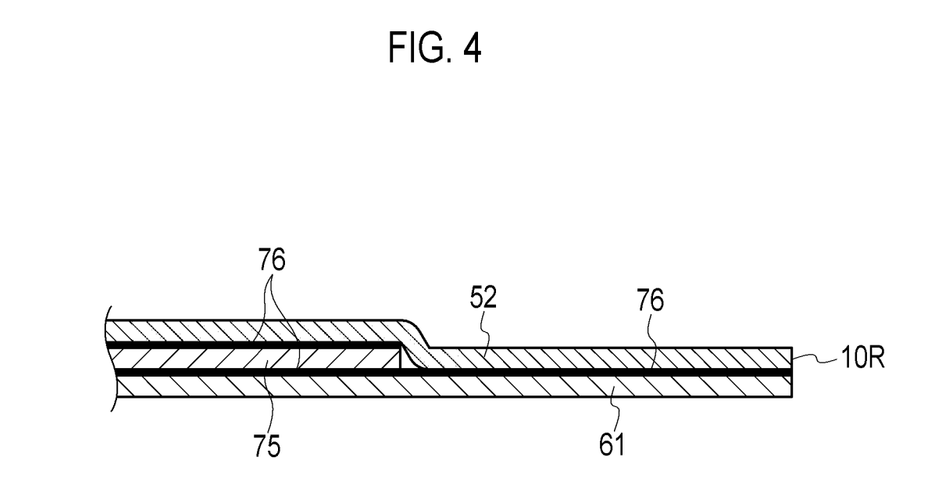
FIG. 4 is a cross-sectional view of the disposable diaper along an F2-F2 line shown in FIG. 1.

FIG. 1 and FIG. 2 are exploded plan views of a disposable diaper 10 according to the present embodiment. FIG. 3 is a cross-sectional view of the disposable diaper 10 along an F1-F1 shown in FIG. 1. FIG. 4 is a cross-sectional view of the disposable diaper 10 along an F2-F2 line shown in FIG. 1. It should be noted that the exploded plan view of FIG. 1 and FIG. 2 are diagram in which leg gathers 75 and leg side gathers 80 are in an expanded state such that wrinkles are not formed in a topsheet 50 and sidesheets 52, for example, that configure the disposable diaper 10, but for the sake of description, the leg side gathers 80 are illustrated in a contracted state.

The disposable diaper 10 includes a front waistline region 20, a crotch region 25, and a rear waistline region 30. The front waistline region 20 is a portion that is in contact with the front waistline (ventral portion) of the wearer. Furthermore, the rear waistline region 30 is a portion that is in contact with the back waistline (dorsal portion) of the wearer. The crotch region 25 is positioned between the front waistline region 20 and the rear waistline region 30. Furthermore, a pair of leg hole openings 35 are formed in the disposable diaper 10. The leg hole openings 35, which are provided at the side ends in the product widthwise direction of the disposable diaper, are the portions that are arranged to fit around the legs of the wearer when the disposable diaper is worn by the wearer.

In the present embodiment, the direction from the front waistline region 20 to the rear waistline region 30 is called a product longitudinal direction L, and the direction perpendicular to the product longitudinal direction L is called a product widthwise direction W.

The disposable diaper 10 includes an absorber 40 running across the crotch region 25 and extending from the crotch region 25 towards at least one of the front waistline region 20 and the rear waistline region 30. The absorber 40 is configured by an absorbent core 40a and a core wrap 40b.

The absorbent core 40a is the same as in the conventional disposable diaper, and can be configured appropriately by using popular components and materials, such as ground pulp and high absorbent polymer. The absorbent core 40a is wrapped by the sheet-like core wrap 40b. The core wrap 40b is a sheet for wrapping the absorbent core 40a. A part of at least the skin surface side of the core wrap 40b is configured by various nonwoven fabric or a tissue sheet having permeability. For example, an air-through nonwoven cloth, a spunbond nonwoven cloth, or an SMS (spunbond-meltblown-spunbond) nonwoven cloth having a mass of approximately 10 to 30 $g/m^2$, or a tissue sheet having a mass of approximately 10 to 30 $g/m^2$ can be used.

On the top side (skin contact surface side) of the absorber 40 is provided a skin-surface side sheet 50. The skin-surface side sheet 50 includes a liquid-permeable topsheet 51 and hydrophobic side sheets 52. The topsheet 51 is arranged to cover almost the entire absorber 40. The side sheets 52 are arranged to cover the side units in the product widthwise direction of the absorber 40 and the topsheet 51. The skin-surface side sheet may not necessarily be configured by the two layers of the topsheet 51 and the side sheets 52, may be configured by either of the two sheets, and with including the other sheet.

On the back side (non-skin contact surface side) of the absorber 40 is provided a liquid-impermeable non-skin surface side sheet 60. The non-skin surface side sheet 60 includes an exterior sheet 61 configuring an outer surface of the disposable diaper at the time of wearing, and a backsheet 62 arranged between the absorber 40 and the exterior sheet 61. The non-skin surface side sheet may not necessarily be configured by the exterior sheet 61 and the backsheet 62, and may be configured by either of the two sheets, and with including the other sheet.

The skin-surface side sheet 50 and the non-skin surface side sheet 60 are joined by a hot-melt adhesive 76 (see FIG. 4). A joint region 65 (see FIG. 2) in which the skin-surface side sheet 50 and the non-skin surface side sheet 60 are joined is provided in the disposable diaper 10. The joint region 65 will be described later in detail.

The side sheets 52 are provided in each of the side edges in the product widthwise direction W of the absorber 40. The side sheets 52 are configured by one layer of nonwoven fabric or two or more plurality of layers of nonwoven fabric layered on each other. Furthermore, a fastening tape 90 is provided in each of the pair of side sheets 52.

The fastening tape 90 extends along the product widthwise direction W in the rear waistline region 30, and holds the disposable diaper 10 onto the body of the wearer when affixed on the non-skin contact surface of the front waistline region 20.

In the present embodiment, a waistline retaining unit is configured by the front waistline region 20, the rear waistline region 30, and the fastening tape 90. The waistline retaining unit of the rear waistline region 30 is the range extending in the widthwise direction from the region provided with an engagement member of the fastening tape 90. The waistline retaining unit of the front waistline region 20 is the range extending in the widthwise direction from the region provided with a target unit 95.

The waistline retaining unit is arranged in the outer side in the product longitudinal direction from the leg stretching units 75. For example, if the leg stretching units overlap the waistline retaining unit, the waistline retaining unit is constricted by the leg stretching units in the product longitudinal direction, and the waistline retaining unit might shift in the product longitudinal direction. However, as the waistline retaining unit is arranged in the outer side in the product longitudinal direction from the leg stretching units and there is no overlapping between the two, the shifting of the waistline retaining unit by the leg stretching units can be prevented.

The leg stretching units 75 are arranged in the outer side of the widthwise direction from the absorber 40. The leg stretching units 75 are arranged on the circumference of the leg hole openings 35, and are configured to be stretchable in the product longitudinal direction L.

Additionally, inside the pair of leg stretching units 75 (closer to the center in the product widthwise direction W), a pair of leg side gathers 80 extending along the product longitudinal direction L are provided. The leg side gathers 80, which are provided in the inner ends in the product widthwise direction of the side sheets 52, are upright stretching gathers arranged in the inner side in the product widthwise direction from the leg stretching units. The leg side gathers 80 are arranged in the inner side in the product widthwise direction from the leg stretching units 75, and function as the leg side stretching units.

The side sheets 52 are folded back at the topsheet side in the inner ends in the product widthwise direction, and are formed by laminating two layers. Elastic members 71 (see FIG. 3) elongated in the longitudinal direction are provided between the two layers of the side sheets 52. The upright leg side gathers 80 are formed by the side sheets 52 and the elastic members 71.

The exploded plan view of the disposable diaper shown in FIG. 1 is the state in which the elastic members 71 of the leg side gathers 80 are in a contracted state, and the exploded plan view of the disposable diaper shown in FIG. 2 illustrates the state in which the elastic members 71 of the leg side gathers 80 are in an elongated state.

The leg side gathers 80 include a joint portion 81 that is joined with either the topsheet 51, or the backsheet 62 and the exterior sheet 61, and a free end portion 82 in which the elastic members are arranged. In the free end portion 82, the central portion in the longitudinal direction that includes the crotch region 25 configures a contraction portion 84 that is constricted in the product longitudinal direction by the elastic members 71. As for the leg side gathers 80, when the diaper is worn, the joint portion 81 rises up as the proximal end and the contraction portion 84 of the free end portion 82 is in contact with the skin of the wearer as the apex. That is, the joint portion is the proximal end of the rise of the leg side stretching units.

The contraction portion 84 is the portion that is substantially constricted in the product longitudinal direction by the elastic members 71, and excludes the portion in which the elastic members 71 are arranged in a state in which the shrinkage force is not exhibited. Furthermore, in FIG. 2, the joint portions 81 in which the side sheets 52 and the topsheet 50, or the backsheet 62 and the exterior sheet 61 are joined in the leg side gathers are marked with slanting lines and illustrated.

Multiple joint portions 81 are provided, and while a first joint portion 81A is arranged in the outer side in the product longitudinal direction from the contraction portion 84, a second joint portion 81B is arranged in the outer side in the product widthwise direction from the contraction portion 84. Thus, in the leg side gathers 80, the central portion in the product longitudinal direction that includes the crotch region 25 is configured to rise up at the side of the wearer.

Of the joint portions 81 of the leg side gathers 80, the second joint portion 81B that is arranged in the outer side in the product widthwise direction from the contraction portion 84 is arranged in the inner side in the product widthwise direction from the leg stretching units 75 in the product widthwise direction W. The second joint portion 81B is joined with the exterior sheet 61 through the backsheet 62 and a part thereof, in the entire length in the product longitudinal direction. The backsheet 62 is arranged between the absorber 40 and the exterior sheet 61, and functions as a leakage-preventing sheet.

Of the joint portions 81 of the leg side gathers 80, the first joint portion 81A that is arranged in the outer side in the product longitudinal direction from the contraction portion 84 is joined with the topsheet 51.

The joint portions 81 of the leg side gathers 80 can have different types of configurations. The joint portions, for example, extend in the front waistline region and the rear waistline region from the inner leg unit in the product longitudinal direction, and are configured to be an upright proximal end that may be the portion joined with the topsheet, or the portion joined with the backsheet and the exterior sheet in the outer side of the widthwise direction from the absorbent core 40a.

Furthermore, the configuration of the leg side gathers is not limited to the above configuration as long as the leg side gathers are upright gathers arranged in the inner side in the product widthwise direction from the leg stretching units, and a configuration of the conventionally well-known leg side gathers can surely be adopted.

Furthermore, a waist stretching unit 85 is provided between the pair of fastening tapes in the product widthwise direction and can expand and contract in the product widthwise direction. The waist stretching unit 85 is arranged between the pair of fastening tapes in a plan view and shrinks the space between the fastening tapes in the widthwise direction. The waist stretching unit 85 is arranged on the surface at the skin contact surface side of the topsheet and shrinks the space between the fastening tapes along the product widthwise direction W.

In the present embodiment, the waist stretching unit 85 is configured by a stretchable sheet. The member configuring the waist stretching unit 85 is not particularly restricted, but a member that is as thin as possible with a low bending rigidity, and has a small reduction in width is preferably used.

In the present embodiment, a stretch film having a basis weight of 20 to 45 g/m$^2$ is used as the waist stretching unit 85.

After being extended up to 1.5 to 2.5 times the length in the non-elongated state (natural state), the waist stretching unit 85 is adhered onto the exterior sheet 61 with a hot-melt adhesive or heat processing.

In the present embodiment, the waist stretching unit 85 is arranged between the backsheet 62 and the exterior sheet 61. However, in the case of a configuration in which the core wrap 40b extends in the outer side in the product longitudinal direction from the absorbent core 40a, the waist stretching unit 85 may be arranged between the core wrap 40b and the backsheet 62 or exterior sheet 61. The position of the waist stretching unit is not particularly restricted, however, the waist stretching unit is preferably arranged at the non-skin contact surface side from the absorber 40. Furthermore, in the region in which the absorber is not arranged, the waist stretching unit may be arranged between the side sheets 52 and the backsheet 62 or exterior sheet 61.

The waist stretching unit according to the present embodiment is configured to stretch in the product widthwise direction, however, the waist stretching unit may be configured to stretch in the product widthwise direction and the product longitudinal direction.

(2) Leg Stretching Units

Next, the leg stretching units 75 will be described in detail. The leg stretching units 75 are arranged along the leg hole openings 35 provided in the outer side in the product widthwise direction from the absorber 40, and are configured to be stretchable in the product longitudinal direction L. In a plan view, the leg stretching units 75 are arranged in the inner side in the product longitudinal direction from the diaper ends that configure the outer circumference of the disposable diaper.

The diaper ends specifically imply front ends 10F of the disposable diaper, back ends 10R of the disposable diaper, and ends 10W in the product widthwise direction of the disposable diaper. The configuration of the present embodiment according to which the leg stretching units 75 are positioned in the inner side in the product longitudinal direction from the diaper ends implies the configuration according to which the leg stretching units 75 are positioned in the inner side in the product longitudinal direction from the front ends 10F and the back ends 10R of the disposable diaper.

Furthermore, for example, when the ends in the in the direction of expansion and contraction of the leg stretching units 75 extend in the product widthwise direction, the leg stretching units 75 are configured to be positioned in the inner side in the product widthwise direction from the diaper ends. Specifically, the leg stretching units 75 are configured to be positioned in the inner side in the product widthwise direction from the ends 10W in the product widthwise direction of the disposable diaper.

The leg stretching units 75 thus configured are arranged only at the necessary locations, such as near the leg hole openings 35, rather than being arranged in the entire region of the diaper. Furthermore, in the case of a configuration in which the leg stretching units 75 shrink in the product longitudinal direction, the outer ends in the product widthwise direction of the leg stretching units 75 may be aligned with the ends in the widthwise direction, such as the side sheets that form the leg hole openings 35. In addition, in the case of a configuration in which the leg stretching units 75 shrink in the product widthwise direction, the outer ends in the product longitudinal direction of the leg stretching units 75 may be aligned with the ends in the longitudinal direction, such as the side sheets that form the diaper ends.

The leg hole openings 35 and the leg stretching units 75 include an inner end region 751 in the widthwise direction that is positioned at the innermost side in the crotch region in the widthwise direction, and extend in the outer side in the product widthwise direction from the crotch region 25 towards the outer side in the product longitudinal direction. It must be noted that the inner end region 751 in the widthwise direction of the leg stretching units 75 may be arranged in continuation in the product longitudinal direction, or may not be in continuation in the product longitudinal direction.

The leg stretching units 75 according to the present embodiment are configured by a stretchable sheet. For example, a stretch film formed by melting a thermoplastic elastomer resin, such as urethane and styrene, and then converting into the shape of a film, a stretchable nonwoven fabric formed from such stretchable fibers, or a composite sheet formed by pasting together inextensible sheets that have been partially cut into a stretch film and stretchable nonwoven fabric, or have been made fragile can be used as the stretchable sheet.

Furthermore, rather than the stretchable sheet, the leg stretching units 75 may be configured by arranging one or a plurality of thread-like or band-like elastic members made of polyurethane elastic fibers and natural rubber.

The leg stretching units 75 are arranged between the skin-surface side sheet 50 and the non-skin surface side sheet 60. Specifically, the leg stretching units 75 are arranged between the side sheets 52 and the exterior sheet 61. Alternatively, in the region provided with the backsheet 62 that is arranged between the absorber 40 and the exterior sheet 61, the leg stretching units 75 are arranged between the backsheet 62 and the side sheets 52.

At least in the crotch region 25, the stretchable sheet configuring the leg stretching units 75 is preferred to have a width of 5 mm (width in the product widthwise direction W in the natural state of the disposable diaper 10) or more and 45 mm or less, or more preferably a width of 12.5 mm or more and 35 mm or less. When the width is less than 5 mm, the effect of lowering of the load on the skin by the elastic elements achieved by substantially running, in the form of a surface of the stretchable sheet, along the area around the legs of the wearer so as to prevent the partial concentration of the securing force is not exhibited, and when the width exceeds 45 mm, the region along the area around the legs becomes too wide in comparison to the length in the product widthwise direction of the entire disposable diaper, and as a result, the stretchable sheet might become entangled at the side of the wearer's body, or may turn over.

The ratio of expansion and contraction of the leg stretching units 75 is preferably 1.5 times to 2.3 times. In the present embodiment, the ratio of expansion and contraction of the leg stretching units 75 is set to 1.8 to 2.0 times. It should be noted that the ratio of expansion and contraction implies the extent of elongation of the leg stretching units and is stipulated as below.

Ratio of expansion and contraction=(Length of the leg stretching units in the elongated state)÷(Length of the leg stretching units in the natural state)

It should be noted that the ratio of expansion and contraction as used herein is to be measured as described below, for example.

Firstly, if the disposable diaper 10 is inserted in a package, for example, then the disposable diaper 10 is taken out of the package, and the diaper is kept in such a condition for 60 minutes under an atmosphere having a temperature of 20° C.±2° C., and a relative humidity of 60%±5% RH, and the length of the leg stretching units is measured along the in the direction of expansion and contraction. This length is the "Length of the leg stretching units in the natural state".

Secondly, the length in the in the direction of expansion and contraction of the desired region of the open-type disposable diaper in this state (that is, in the natural state), and the length in the in the direction of expansion and contraction of the desired region, when the open-type disposable diaper is extended from its natural state until wrinkles caused by the elastic members are not visible, are measured. This length is the "Length of the leg stretching units in the elongated state".

The ratio of expansion and contraction is measured by using these measurement results and calculating according to the formula described above.

Additionally, it is preferable to measure the length in each of the above-described states along the lines at the ends inside in the product widthwise direction of the leg stretching units when the leg stretching units are curved as in the present embodiment.

Furthermore, the interval between the inner ends of the pair of the left-right leg stretching units 75 in the product widthwise direction W widens from the crotch region 25 towards the front waistline region 20, and also widens from the crotch region 25 towards the rear waistline region 30. When the diaper is worn on the body of the wearer, if the leg stretching units are arranged in a shape that is narrow in the crotch and broadens towards the front and back waistline, the leg stretching units can be brought closer along the line of the body, and the leg stretching units are elongated and arranged favorably in the area around the legs of the wearer.

Additionally, the interval (D1 in the figure) between the ends of the front waistline region 20 of the pair of left-right leg stretching units 75 is narrower than the interval (D2 in the figure) between the ends of the rear waistline region 30 of the pair of left-right leg stretching units 75. The interval is the distance between the inner ends of the pair of left-right leg stretching units 75 in the product widthwise direction W that is measured after expanding and holding the disposable diaper 10 from the natural state to the state when no wrinkles are formed, in the product longitudinal direction L and the product widthwise direction W.

The extension of the skin surface of the body of the wearer is particularly large in the hip, and is remarkable at a position towards the outer widthwise direction. Furthermore, the leg stretching units 75 are in contact with the body of the wearer. Because D2>D1, even when the movement of the wearer is added to the disposable diaper 10, the leg stretching units 75 in the hip can extend while being in contact with the body, and even when the amount of change of the stretching is large, the leg stretching units 75 do not become stiff. Therefore, the shifting of the disposable diaper 10 by the leg stretching units 75 can be controlled.

Furthermore, the leg hole openings 35 and the leg stretching units 75 have a curved shape that extends in the outer side in the product widthwise direction from the crotch region 25 towards the outer side in the product longitudinal direction, and the distance between the inner ends in the product widthwise direction at the ends in the product longitudinal direction of the leg stretching units 75 and the inner ends in the product widthwise direction in the crotch region of the leg stretching units is 3 mm or more and 35 mm or less.

Specifically, as shown in FIG. 2 a distance D3 between inner ends 75RW in the product widthwise direction at the back ends of the leg stretching units, and inner ends 75CW in the product widthwise direction at the portion positioned in the innermost side of the widthwise direction of the leg stretching units, or a distance D4 between inner ends 75FW in the product widthwise direction at the front ends of the leg stretching units, and the inner ends 75CW in the product widthwise direction at the portion positioned in the innermost side of the widthwise direction of the leg stretching units is 3 mm or more and 35 mm or less.

It should be noted that as long as the leg hole openings 35 are configured to be stretchable in the product longitudinal direction, the leg stretching units 75 may be arranged along the leg hole openings 35, a part of the leg stretching units may be arranged at a slant with respect to the leg hole openings 35, or a part of the leg stretching units may be spaced apart from the leg hole openings 35. Specifically, the distance between the leg hole openings 35 and the leg stretching units 75 in the product widthwise direction is desired to be 7 mm or less. This is because when the distance between the leg hole openings 35 and the leg stretching units 75 in the product widthwise direction is 7 mm or less, the stretching force of the leg stretching units 75 is substantially transferred up to the leg hole openings 35, and the diaper can be affixed on the wearer up to the ends of the leg hole openings 35.

It should be noted that the leg stretching units 75 correspond to the portion that is substantially constricted in the product longitudinal direction by the stretchable sheet and the thread-like elastic members, and exclude the portion in which the stretchable sheet is arranged in a state in which the contraction force is not exhibited.

(3) Configuration of Joint Region

Next, the joint region 65 will be described. The joint region 65 is the region where the skin-surface side sheet 50 and the non-skin surface side sheet 60 are joined by a hot-melt adhesive, or the like. In FIG. 2, the joint region 65 is illustrated by adding slanting lines. The joint region 65 illustrated in FIG. 2 is the region in which the skin-surface side sheet 50 and the non-skin surface side sheet 60 are pasted directly.

The joint region 65 is arranged at least in a first region (see FIG. 1) R1 in the outer side in the product longitudinal direction from the ends in the product longitudinal direction of the leg stretching units, and a second region (see FIG. 1) R2 in the outer side in the product widthwise direction from the ends in the product longitudinal direction of the leg stretching units.

In the first region R1 and the second region R2, the joint region 65 where the skin-surface side sheet 50 and the non-skin surface side sheet 60 are joined is provided in continuation along the diaper ends. Specifically, in the first region R1, the joint region 65 is provided in continuation in the product widthwise direction along the front ends 10F of the disposable diaper and the back ends 10R of the disposable diaper. Furthermore, in the second region R2, the joint region 65 is provided in continuation in the product longitudinal direction along the ends 10W in the product widthwise direction of the disposable diaper.

Furthermore, in the first region R1, a part of the waistline retaining unit, which is arranged inside the region extending along the product widthwise direction from the fastening tape 90 and is arranged inside the region extending along the product widthwise direction from the target unit 95, is arranged.

In this way, as the joint region 65 is provided in continuation along the diaper ends in the first region R1 and the second region R2, the strength can be increased as compared to the configuration in which sheets are not joined together. A part of the waistline retaining unit is arranged in the first region R1 and the second region R2, which forms the region where force is exerted at the time of wearing the diaper. By increasing the strength of this region, the tearing of the sheets can be prevented when a relatively high load is exerted, such as at the time of putting on or wearing the diaper.

Furthermore, in the entire disposable diaper, as seen in the plan view, the skin-surface side sheet 50 and the non-skin surface side sheet 60 are joined with each other through another member (such as a fastening tape). Thus, the joint region is substantially provided in continuation along the diaper ends in the entire region of the disposable diaper.

Specifically, in the portion where the fastening tape is arranged, the skin-surface side sheet and the non-skin surface side sheet are pasted through the fastening tape, and in the portion where the absorber is arranged, the skin-surface side sheet and the non-skin surface side sheet are pasted through the absorber, and furthermore, in the portion where the leg stretching units 75 are arranged, the skin-surface side sheet and the non-skin surface side sheet are pasted through the leg stretching units 75.

Because the joint region is arranged in the entire region of the disposable diaper, the rigidity of the entire disposable diaper and the strength of the disposable diaper can be increased. Furthermore, if the topsheet and the backsheet are spaced apart in a part of the ends of the diaper, the user may feel that the product is defective, and may be concerned about leakage from the portion where the topsheet and the backsheet are spaced apart. However, as the joint region is provided in the entire region of the disposable diaper, the disposable diaper can be worn by the wearer without any concerns.

The joint region is not only configured by the region where the skin-surface side sheet and the non-skin surface side sheet are joined by direct contact, but also includes the configuration where the skin-surface side sheet and the non-skin surface side sheet are joined through another member (such as a sheet). Furthermore, in the joint region, the two layers of the skin-surface side sheet in the form of the side sheets or the topsheet, and the non-skin surface side sheet in the form of the backsheet or the exterior sheet may be joined together, or a plurality of layers of the skin-surface side sheet, and a plurality of layers of the non-skin surface side sheet may be joined together. In addition, the joint region may be the region where the sheets are joined together by a hot-melt adhesive, or may be a region where joining is performed by another joining method such as heat welding, etc.

(4) Method of Manufacturing the Disposable Diaper

Next, an example of the method of manufacturing the disposable diaper according to the present embodiment will be described. As far as the method that is not described in the present embodiment is concerned, the existing method can be used. Furthermore, the manufacturing method explained below is only an example, and the disposable diaper can also be manufactured by other manufacturing methods. The method of manufacturing the disposable diaper includes at least a component forming step, a component loading step, a leg hole forming step, and a cutting step.

In the component forming step, the components configuring the disposable diaper are formed. Specifically, for example, an absorbent material is laminated and the absorber 40 is molded.

The component loading step includes loading on a first web, which configures one of the skin-surface side sheet and the non-skin surface side sheet, the components configuring the disposable diaper, such as the stretchable sheet that configures the leg stretching units 75, the second web that configures the other one of the skin-surface side sheet and the non-skin surface side sheet, etc.

More specifically, a step of continuously conveying a first web, a step of elongating the elastic members configuring the leg stretching units in a continuous state, in the product longitudinal direction, a step of cutting the elastic members that are in the elongated state along the product widthwise direction, a step of pasting the elastic members that are in the cut state on the first web through an adhesive, and a step of affixing the second web on the first web and the elastic members through an adhesive are included.

For example, the step of elongating the elastic members configuring the leg stretching units in a continuous state, in the product longitudinal direction, and the step of cutting the same are implemented by elongating the stretchable sheet that configures the leg stretching units 75, transferring the stretchable sheet onto an intermittent drum while displacing in the widthwise direction, and then cutting the stretchable sheet in individual product lengths on the intermittent drum. Furthermore, a gap is provided between the stretchable sheets as a result of the rotation of the intermittent drum, and the stretchable sheets are transferred on a continuous web. At this time, the stretchable sheet and the web are affixed by applying an adhesive beforehand either on the stretchable sheet or the web. Next, another web is affixed to the web on which the stretchable sheet has been affixed. At this time, by applying an adhesive on at least any one of the first web or the second web, the first web, the stretchable sheet, and the second web can be joined together as one part.

It should be noted that if the adhesive is to be applied on both the first web and the second web, it is desirable to have different adhesion patterns for the first web and the second web. Generally, when applying the adhesive, an interval is provided such as by applying the adhesive in helices or dots. At this time, for example, if the pattern of applying the adhesive on the first web and the second web is the same, then when the non-joint portions, where an adhesive is not applied, are aligned, the non joint portions will be aligned at several locations as the non-joint portions are also arranged at the same interval. This would lead to the presence of several non joint portions.

However, by changing the pattern of application of the adhesive on the first web and the second web, even when the non joint portions are aligned in one part, the alignment of the non joint portions at several locations can be prevented as the non-joint portions are arranged at a different interval. Thus, skipping of the leg stretching units in the non joint portions, and isolation of sheets can be prevented.

In the leg hole forming step, the first web that configures the skin-surface side sheet 50 and the second web exterior sheet that configures the non-skin surface side sheet 60 are cut along the outer ends of the widthwise direction of the leg stretching units 75. The leg hole openings 35 arranged in the area around the legs of the wearer are thus formed.

In the cutting step, the continuous body on which the topsheet 51, the exterior sheet 61, and the absorber 40 are arranged is cut in the size of one product along the product widthwise direction W. The disposable diaper 10 is thus manufactured.

According to such a manufacturing method, there is no need of providing a non-adhering portion for stretching the leg stretching units after cutting the web as in the past, and therefore, the skin-surface side sheet 50 and the non-skin surface side sheet 60 can be joined in the first region R1 and the second region R2 in the circumference of the leg stretching units 75 while arranging the leg stretching units only near the leg hole openings 35. In comparison to the configuration where the sheets are not joined with each other, as in the past, the strength of the sheets can be increased. A part of the waistline retaining unit is arranged in the first region and the second region, and this is the region where force is exerted at the time of wearing the diaper. By increasing the strength of this region, the tearing of the skin-surface side sheet 50 and the non-skin surface side sheet 60 at the time of wearing the diaper can be prevented.

Furthermore, in the disposable diaper according to the modification, rather than leg gathers formed from an elastic nonwoven sheet, leg gathers formed from thread-like elastic members may be provided.

(5) Operation and Effect

In the disposable diaper according to the present embodiment, the first region R1 and the second region R2 that are arranged in the circumference of the ends in the in the direction of expansion and contraction of the leg stretching units 75 can be joined when the leg stretching units 75 are arranged only near the leg hole openings 35. Therefore, in comparison to the configuration where the sheets are not joined with each other, the strength of the sheets can be increased. A part of the waistline retaining unit is arranged in the first region and the second region, and this is the region where force is exerted at the time of wearing the diaper. By increasing the strength of this region, the tearing of the skin-surface side sheet and the non-skin surface side sheet at the time of wearing the diaper can be prevented.

Furthermore, the skin-surface side sheet and the non-skin surface side sheet are substantially joined in the entire region of the disposable diaper. Thus, the rigidity of the entire disposable diaper can be improved. Furthermore, if the skin-surface side sheet and the non-skin surface side sheet are spaced apart in a part of the ends of the diaper, the user may feel that the product is defective. However, as the joint region is provided in the entire region of the disposable diaper, the disposable diaper can be worn by the wearer without any concerns.

The skin-surface side sheet 50 arranged in the first region R1 and the second region R2 can be configured only by a nonwoven fabric having a basis weight of 15 g/m$^2$ or less. The strength of the disposable diaper 10 according to the present embodiment can be increased by joining the skin-surface side sheet 50 and the non-skin surface side sheet 60. Thus, the skin-surface side sheet 50 can be configured only by a nonwoven fabric, without including a film such as a leakage-preventing film having a relatively high rigidity. By configuring the skin-surface side sheet 50 only by a non-woven fabric, and by being able to reduce the basis weight of the nonwoven fabric, the feel on the skin can be made softer and the air permeability of the corresponding part can be improved. It should be noted that the non-skin surface side sheet 60 may be configured only by a nonwoven fabric.

(6) Other Embodiments

As described above, the present invention is disclosed through the above embodiments of the present invention. However, it should not be interpreted that the statements and drawings constituting a part of the present disclosure limit the present invention. From this disclosure, a variety of alternate embodiments, examples, and applicable techniques will become apparent to one skilled in the art.

For example, in the method of manufacturing the disposable diaper, the step of elongating the cut elastic members in the product longitudinal direction may be performed after the step of cutting the elastic members configuring the leg stretching units along the product widthwise direction.

As described above, it is of course that the present invention includes various embodiments and the like not described here. Therefore, the technical range of the present invention is to be defined only by the inventive specific matter according to the adequate claims from the above description.

The entire contents of Japanese Patent Application No. 2012-103376 (filed on Apr. 27, 2012) are incorporated in the present specification by reference.

INDUSTRIAL APPLICABILITY

It is possible to provide a disposable diaper with which the strength of the waistline retaining unit that holds the waistline of the wearer in a so-called tape-type disposable diaper is increased, and the tearing at the time of putting on or wearing the diaper can be prevented, and also to provide a method of manufacturing such a disposable diaper.

REFERENCE SIGNS LIST

10 . . . Disposable diaper
10F . . . Front end
10R . . . Back end
10W . . . Ends in the product widthwise direction
20 . . . Front waistline region
25 . . . Crotch region
30 . . . Rear waistline region
35 . . . Leg hole opening
40 . . . Absorber
40*a* . . . Absorbent core
40*b* . . . Core wrap
50 . . . Skin-surface side sheet
51 . . . Topsheet
52 . . . Side sheet
60 . . . Non-skin surface side sheet
61 . . . Exterior sheet
62 . . . Backsheet
65 . . . Joint region 71 . . . Elastic member
75 . . . Leg stretching unit
75I . . . Inner end region in the widthwise direction of the leg stretching units
80 . . . Leg side gather
81 . . . joint portion
81A . . . First joint portion
81B . . . Second joint portion
82 . . . Free end portion
84 . . . Contraction portion
85 . . . Waist stretching unit
90 . . . Fastening tape
95 . . . Target unit
L . . . Product longitudinal direction
W . . . Product widthwise direction
R1 . . . First region
R2 . . . Second region

The invention claimed is:

1. A disposable diaper, comprising:
   a front waistline region, a rear waistline region, a crotch region positioned between the front waistline region and the rear waistline region;
   a product longitudinal direction from the front waistline region towards the rear waistline region, and a product widthwise direction perpendicular to the product longitudinal direction;
   a skin-surface side sheet adapted to face toward a body of a wearer when the diaper is worn;
   a non-skin surface side sheet adapted to face away from the body of the wearer when the diaper is worn;
   an absorber arranged between the skin-surface side sheet and the non-skin surface side sheet, running across the crotch region in the product longitudinal direction, and extending from the crotch region to at least either one of the front waistline region and rear waistline region;
   a waistline retaining unit disposed in the front and rear waistline regions and adapted to hold the disposable diaper onto the body of the wearer;
   leg stretching units arranged along leg hole openings provided on an outer side of the absorber in the product widthwise direction, said leg stretching unit being configured to expand and contract along the product longitudinal direction; and
   diaper ends defining an outer circumference of the disposable diaper,
   wherein
   the leg stretching units are arranged between the skin-surface side sheet and the non-skin surface side sheet,
   in a plan view of the disposable diaper, the leg stretching units are arranged on an inner side of the diaper ends in the product longitudinal direction or on the inner side of the diaper ends in the product widthwise direction,
   the leg stretching units have ends opposing each other in the product longitudinal direction,
   a part of the waistline retaining unit is arranged in at least one of
      a first region on an outer side in the product longitudinal direction from the ends of the leg stretching units, or
      a second region on an outer side in the product widthwise direction from the ends of the leg stretching units,
   a joint region where the skin-surface side sheet and the non-skin surface side sheet are joined is provided along the diaper ends in at least one of the first region or the second region,
   a first adhesive is applied at an interval, on the skin-surface side sheet of the first region and the second region, based on a first application pattern, and
   a second adhesive is applied at an interval, on the non-skin surface side sheet of the first region and the second region, based on a second application pattern different from the first application pattern.

2. The disposable diaper according to claim 1, wherein the joint region is provided along the diaper ends in an entire area of the disposable diaper.

3. The disposable diaper according to claim 1, wherein the skin-surface side sheet and the non-skin surface side sheet arranged in the first region and the second region are configured only by a nonwoven fabric.

4. The disposable diaper according to claim 1, wherein at least any one of the skin-surface side sheet and the non-skin surface side sheet is configured only by a nonwoven fabric having a basis weight of 15 g/m$^2$ or less.

5. The disposable diaper according to claim 1, wherein
   the leg hole openings and the leg stretching units have a curved shape that extends outward in the product widthwise direction while extending from the crotch region towards the front and rear waistline regions in the product longitudinal direction,
   each of the leg stretching units has
      front and rear inner edges in the product widthwise direction at the ends of the leg stretching unit, and
      an intermediate inner edge in the product widthwise direction in the crotch region, and
   a distance between the first inner edge or the second inner edge and the intermediate inner edge in the product widthwise direction is 3 mm or more and 35 mm or less.

6. The disposable diaper according to claim 1, wherein
   the leg stretching units are band-shaped elastic members each having a predetermined width in the product widthwise direction, and
   the width of each of the elastic members in the product widthwise direction is 5 mm or more and 45 mm or less.

7. The disposable diaper according to claim 1, wherein the waistline retaining unit is arranged on the outer side from the leg stretching units in the product longitudinal direction.

8. The disposable diaper according to claim 1, wherein the part of the waistline retaining unit is arranged in (i) the first region on the outer side in the product longitudinal direction from the ends of the leg stretching units and (ii) the second region on the outer side in the product widthwise direction from the ends of the leg stretching units.

9. The disposable diaper according to claim 8, wherein the joint region where the skin-surface side sheet and the non-skin surface side sheet are joined is provided along the diaper ends in both of the first region and the second region.

10. A disposable diaper, comprising:
    a front waistline region, a rear waistline region, a crotch region positioned between the front waistline region and the rear waistline region;
    a product longitudinal direction from the front waistline region towards the rear waistline region, and a product widthwise direction perpendicular to the product longitudinal direction;
    a skin-surface side sheet adapted to face toward a body of a wearer when the diaper is worn;
    a non-skin surface side sheet adapted to face away from the body of the wearer when the diaper is worn;

an absorber arranged between the skin-surface side sheet and the non-skin surface side sheet, running across the crotch region in the product longitudinal direction, and extending from the crotch region to at least either one of the front waistline region and rear waistline region;

a waistline retaining unit disposed in the front and rear waistline regions and adapted to hold the disposable diaper onto the body of the wearer;

leg stretching units arranged along leg hole openings provided on an outer side of the absorber in the product widthwise direction, said leg stretching unit being configured to expand and contract along the product longitudinal direction; and diaper ends defining an outer circumference of the disposable diaper, wherein the leg stretching units are arranged between the skin-surface side sheet and the non-skin surface side sheet, in a plan view of the disposable diaper, the leg stretching units are arranged on an inner side of the diaper ends in the product longitudinal direction or on the inner side of the diaper ends in the product widthwise direction, the leg stretching units have ends opposing each other in the product longitudinal direction, a part of the waistline retaining unit is arranged in at least one of
- a first region on an outer side in the product longitudinal direction from the ends of the leg stretching units, or
- a second region on an outer side in the product widthwise direction from the ends of the leg stretching units, a joint region where the skin-surface side sheet and the non-skin surface side sheet are joined is provided along the diaper ends in at least one of the first region or the second region, a first adhesive is applied in a first application pattern, on the skin-surface side sheet of the first region and the second region, and a second adhesive is applied in a second application pattern, on the non-skin surface side sheet of the first region and the second region, the second application pattern different from the first application pattern.

* * * * *